(12) United States Patent
Mabry et al.

(10) Patent No.: US 9,315,527 B2
(45) Date of Patent: Apr. 19, 2016

(54) SYNTHESIS AND APPLICATIONS OF PERIPHERALLY ASYMMETRIC ARYL POSS COMPOUNDS

(71) Applicant: The United States of America as Represented by the Secretary of the Air Force, Washington, DC (US)

(72) Inventors: Joseph M. Mabry, Lancaster, CA (US); Brian M. Moore, Surry, NH (US); Sean Ramirez, San Diego, CA (US); Gregory R. Yandek, Tehachapi, CA (US)

(73) Assignee: The United States of America as requested by the Secretary of the Air Force, Washington, DC (US)

( * ) Notice: Subject to any disclaimer, the term of this patent is extended or adjusted under 35 U.S.C. 154(b) by 0 days.

(21) Appl. No.: 14/662,305

(22) Filed: Mar. 19, 2015

(65) Prior Publication Data

US 2015/0239915 A1    Aug. 27, 2015

Related U.S. Application Data

(62) Division of application No. 13/624,355, filed on Sep. 21, 2012, now Pat. No. 9,012,673.

(60) Provisional application No. 61/537,125, filed on Sep. 21, 2011.

(51) Int. Cl.
  *C07F 7/21* (2006.01)
  *C09D 5/16* (2006.01)
  *C08G 77/04* (2006.01)
  *C08L 83/06* (2006.01)

(52) U.S. Cl.
  CPC .............. *C07F 7/21* (2013.01); *C08G 77/045* (2013.01); *C08L 83/06* (2013.01); *C09D 5/1662* (2013.01)

(58) Field of Classification Search
  USPC ................................................ 556/460, 461
  See application file for complete search history.

(56) References Cited

PUBLICATIONS

Moore; Abstracts of Papers, 241st ACS National Meeting &Exposition, Anaheim, CA, United States, Mar. 27-31, 2011 (2011), POLY-225. American Chemical Society: Washington, D. C.*
Moore; Journal of Organometallic Chemistry 696 (2011) 2676-2680; published on Jul. 1, 2011.*

* cited by examiner

*Primary Examiner* — Sudhakar Katakam
*Assistant Examiner* — Pancham Bakshi
(74) *Attorney, Agent, or Firm* — AFMCLO/JAZ; Chastity Whitaker

(57) ABSTRACT

A method of synthesizing peripherally asymmetric aryl polyhedral oligomeric silsesquioxane (ArPOSS) compounds. The method comprises:

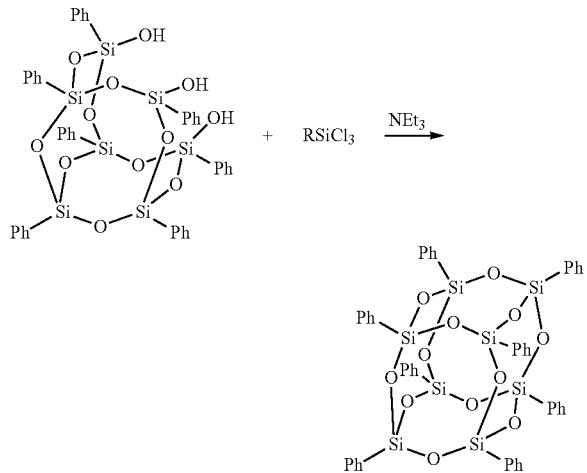

wherein Ph is phenyl and wherein R is 1-napthyl, 2-naphthyl, 9-anthracenyl, 9-phenanthrenyl, 1-pryenyl, and mixtures thereof.

16 Claims, 3 Drawing Sheets

SYNTHESIS AND APPLICATIONS OF PERIPHERALLY ASYMMETRIC ARYL POSS COMPOUNDS

CROSS REFERENCE TO RELATED APPLICATION

This application claims the benefit of and priority to U.S. Provisional Application No. 61/537,125, filed Sep. 21, 2011, and is a divisional application of U.S. application Ser. No. 13/624,355, filed Sep. 21, 2012. The disclosure of each reference is incorporated herein, its entirety.

RIGHTS OF THE GOVERNMENT

The invention described herein may be manufactured and used by or for the Government of the United States for all governmental purposes without the payment of any royalty thereon.

FIELD OF THE INVENTION

This invention relates to synthesis methods and applications for the production and use of organic/inorganic hybrid polyhedral oligomeric silsesquioxane (POSS) nanomaterials.

BACKGROUND OF THE INVENTION

The synthesis of hybrid organic-inorganic materials that combine the diversity and ease of processing of organic polymers with the thermo-chemical stability and oxidative resistance of ceramics remains a goal of material researchers worldwide. Polyhedral Oligomeric SilSesquioxanes (POSS) have emerged as effective multi-functional, highly tailorable additives, capable of improving polymer performance. Each of these nanoparticles features an inorganic $SiO_{1.5}$ core, as well as an organic corona, which helps to determine overall solubility. Compounds based on this architectural framework have received a great deal of attention as nearly ideal hybrid materials due to the synergy of the silsesquioxane cage and organic character at the molecular level.

In contrast to most other forms of nanoscale reinforcement, POSS compounds have been shown to improve processing characteristics when either blended into polymer hosts or incorporated by copolymerization. Although both techniques have distinct advantages, inert blending is generally the preferred method, offering facile modification of commercial polymers without the necessity for polymer synthesis and balancing stoichiometry. Furthermore, blending techniques generally provide access to a greater material design space in the context of nanoparticle assembly. However, the availability of thermally stable, inert POSS additives for the purpose of reinforcing high temperature polymers by this method is limited. Further development would be of benefit to a range of potential products requiring lightweight materials for energy efficiency, aerospace, and durable infrastructure applications.

Aryl-functionalized silsesquioxanes, such as $phenyl_8Si_8O_{12}$ ($Ph_8Si_8O_{12}$), have been in existence for decades, appearing well suited for the preparation of high-performance, aromatic nanocomposites. However, the high symmetry and low dipole moments of $Ph_8Si_8O_{12}$ promote highly-efficient crystalline packing. This is manifested in poor solubility in organic solvents, and a neutral response to mechanical shear, thus severely limiting incorporation into polymers.

To circumvent these limitations, several research groups have focused on the modification of aryl-functionalized POSS compounds. For example, $vinyl_8Si_8O_{12}$ was functionalized with aromatic photo-luminescent compounds via Heck coupling. (Para-iodophenyl)$_8Si_8O_{12}$ was synthesized as a platform for coupling additional organic moieties to POSS cages. Other work attached $Ph_8Si_8O_{12}$ to polybenzimidazole via an in-situ Friedel-Crafts acylation copolymerization reaction. Researchers have found that copolymerized $Ph_8Si_8O_{12}$ was more thoroughly dispersed in the polymer host than physically blended $Ph_8Si_8O_{12}$.

Unfortunately, none of the above methods have proven to be fully successful in overcoming the limitations of non-reactive, aryl-functionalized POSS compounds such as poor solubility in organic solvents, and a neutral response to mechanical shear. There remains a need for aryl-functionalized POSS compounds which overcome these limitations.

SUMMARY OF THE INVENTION

Applicants have discovered peripherally asymmetric aryl polyhedral oligomeric silsesquioxane (ArPOSS) compounds, synthesized by "corner-capping" methodology, which overcome the limitations of $Ph_8Si_8O_{12}$ through geometric consideration of the POSS cage periphery. Synthesis of these compounds proceeds through a capping reaction with uncondensed phenyl POSS alcohols using trichlorosilanes with terminal aryl groups that are geometrically larger in size than phenyl groups, such as naphthalene, anthracene, penanthrene, and pyrene. These corner-capped POSS compounds demonstrate enhanced solubility in organic solvents and aromatic polymers, enabling a more facile route to the fabrication of high temperature nanocomposites, without conciliating absolute peripheral aromaticity thus retaining superior thermal stability.

DETAILED DESCRIPTION OF THE INVENTION

Figure 1:
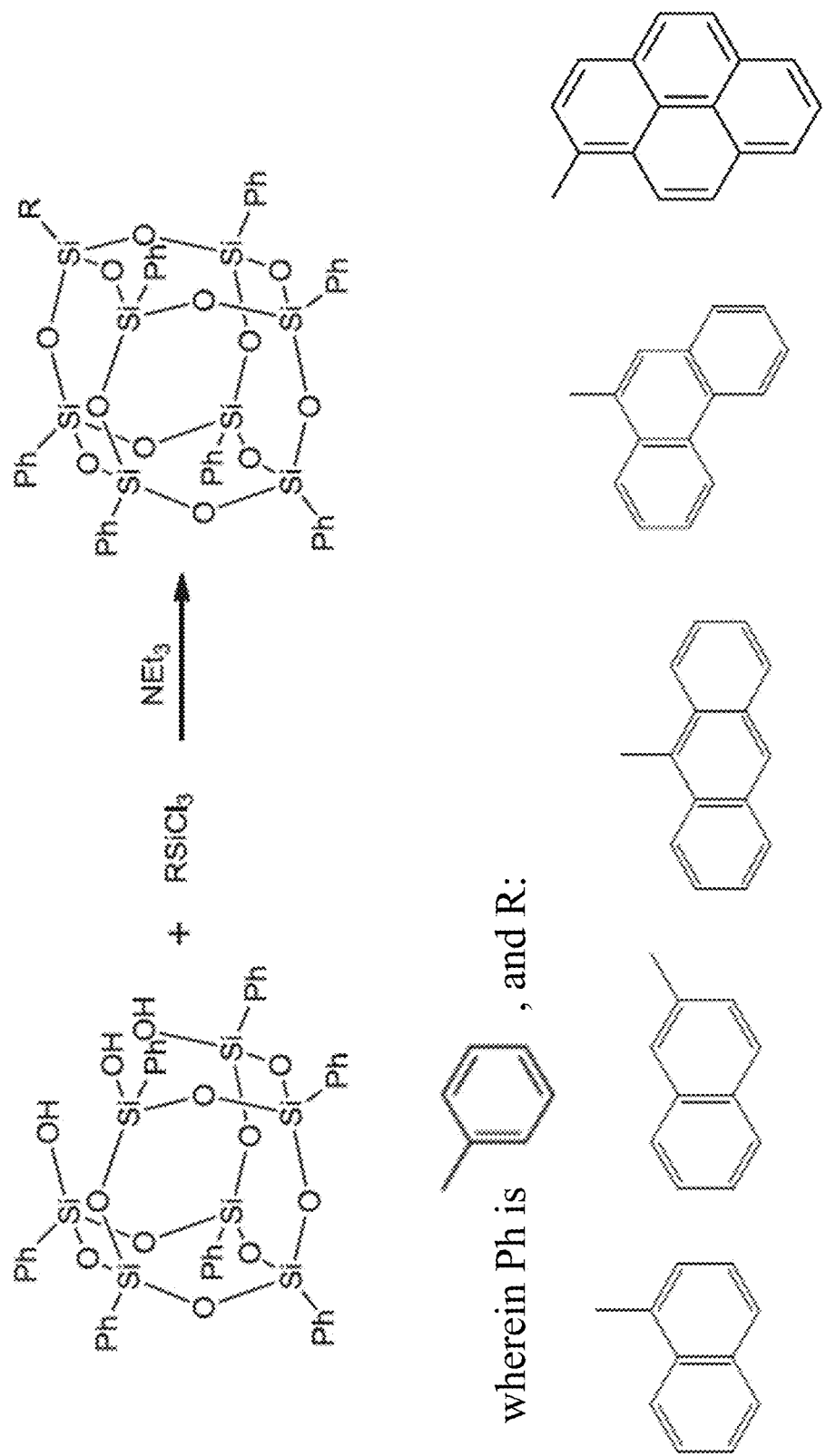
FIG. 1 shows the synthesis of corner-capped POSS cages.

This invention describes Aromatic POSS structures synthesized by the "corner capping" of $phenyl_7Si_7O_9(OH)_3$ with aryl trichlorosilanes. The desired aryl trichlorosilanes were synthesized by reaction of an aryl Grignard or lithium reagent with $SiCl_4$ under reaction conditions similar to those previously reported. See, e.g., S. D. Rosenberg, J. J. Walburn, H. E. Ramsden, Journal Organomet. Chem. 22 (1957) pages 1606-1607, incorporated herein by reference. The aryl trichlorosilanes ($ArSiCl_3$) (Ar=1-naphthlyl, 2-naphthyl, 9-Anthracethrenyl, 9-phenanthrenyl, and 1-pyrenyl) were coupled with $phenyl_7Si_7O_9(OH)_3$ under basic conditions to yield the desired, well-defined (Aryl)$phenyl_7Si_8O_{12}$ structures as shown in FIG. 1.

The resulting peripherally asymmetric aryl polyhedral oligomeric silsesquioxane (ArPOSS) compounds have the chemical structure:

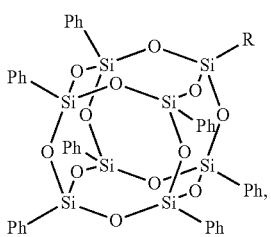

wherein Ph is

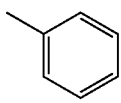

(phenyl) and wherein R is selected from the group consisting of:

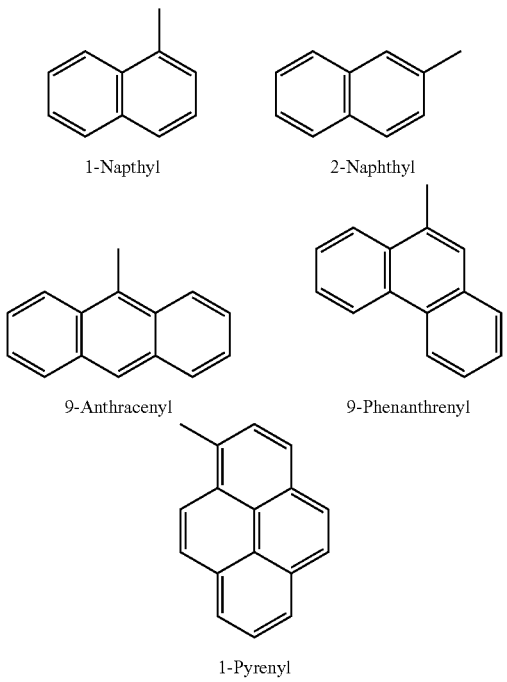

and mixtures thereof.

The preferred compounds include: (1-Naphthyl)phenyl$_7$Si$_8$O$_{12}$, (2-Naphthyl)-phenyl$_7$Si$_8$O$_{12}$, (9-Anthracethrenyl)phenyl$_7$Si$_8$O$_{12}$, (9-Phenanthrenyl)phenyl$_7$Si$_8$O$_{12}$ and (1-Pyrenyl)phenyl$_7$Si$_8$O$_{12}$.

Figure 2:
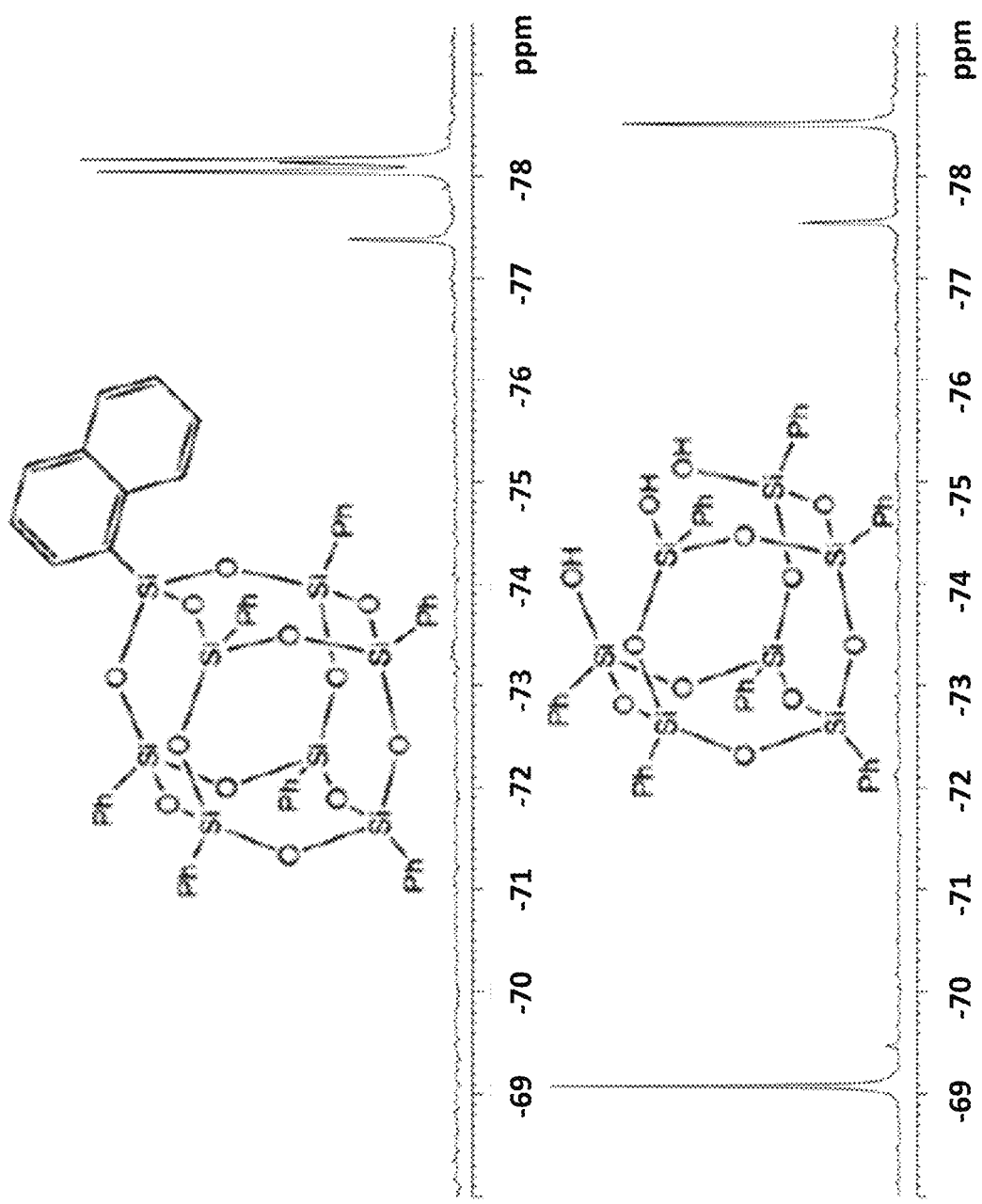
FIG. 2 compares the NMR spectrum of symmetric $phenyl_8Si_8O_{12}$ with peripherally asymmetric (1-naphthyl)$phenyl_7Si_8O_{12}$.

The desired products of these reactions were separated from by-products and starting materials via filtration and methanol washings. Previous work has proven this synthetic strategy as an effective technique for coupling trichlorosilanes to silanols. See, e.g., J. D. Lichtenhan, Y. A. Otonari, M. J. Can, *Macromolecules* 29 (1995) pages 8435-8437, incorporated herein by reference. These POSS cage structures were confirmed on the basis of multinuclear NMR ($^1$H, $^{13}$C, and $^{29}$Si) and elemental combustion analysis (CHN). The absence of silanol NMR peaks was used to confirm reaction completion. The initial chemical shifts of the $^{29}$Si NMR peaks for phenyl$_7$Si$_7$O$_9$(OH)$_3$ are −69.08, −77.54, and −78.51 ppm, respectively, in a ratio of 3:1:3. For comparison, the chemical shift of the single peak for symmetric phenyl$_8$Si$_8$O$_{12}$ is −78.07 ppm. When the corner-capping reaction is complete on the asymmetric compounds, the $^{29}$Si NMR peaks are shifted with respect to the additional substituent aryl group. For example, the peaks of (1-naphthyl)phenyl$_7$Si$_8$O$_{12}$ are shifted to 77.37, −78.05, −78.14, and −78.17 ppm, respectively, in a ratio of 1:3:1:3, as shown in FIG. 2. Similar peak shifts in $^{29}$Si NMR spectra were observed for the remaining corner-capped compounds, though the order of peak integration is occasionally different.

The influence of the prescribed peripheral asymmetry of these compounds on solubility was determined by visual measurements in five organic solvents, including chloroform (CHCl$_3$), tetrahydrofuran (THF), phenyl ether (PE), toluene (Tol), and dimethyl formamide (DMF), summarized in Table 1.

The poor solubility of symmetric phenyl$_8$Si$_8$O$_{12}$ (2) has been previously documented exhibiting only limited solubility (about 1 mg/mL) in CHCl$_3$ and thus, serving as the benchmark for this work. The substitution of a single polycyclic aromatic ring on the POSS cage improves solubility substantially in most cases. However, it is difficult to predict the influence of each aromatic group on the observed solubility, as well as in which solvent the solubility will be affected. Modification with a 1-naphthyl group to produce (1-naphthyl)-phenyl$_7$Si$_8$O$_{12}$ (3) results in solubility in CHCl$_3$ and THF exceeding 100 mg/mL and the observance of more finite solubility in the other investigated solvents. Modification with a 2-naphthyl group to produce (2-naphthyl)phenyl$_7$Si$_8$O$_{12}$ (4) increases solubility in PE and DMF, but reduces solubility in THF and CHCl$_3$, when compared to (1-naphthyl)-phenyl$_7$Si$_8$O$_{12}$ (3). Substitution with a phenanthrenyl group to produce (9-phenanthrenyl)-phenyl$_7$Si$_8$O$_{12}$ (5) results in comparable solubility in THF to that of phenyl$_8$Si$_8$O$_{12}$ (2), as well as the highest solubility in DMF and toluene of any compound examined. Limited solubility gains in comparison with the other polycyclic aromatic groups are observed with pyrenyl substitution, with (1-pyrenyl)phenyl$_7$Si$_8$O$_{12}$ (6) exhibiting the lowest solubility of the four corner-capped POSS cages in the examined solvents, albeit a noteworthy improvement over that of phenyl$_8$Si$_8$O$_{12}$ (2).

TABLE 1

Solubility (mg/mL) of aromatic POSS compounds in organic solvents

| # | CHCl$_3$ | THF | PE | Tol | DMF |
|---|---|---|---|---|---|
| 2 | 1 | $a$ | $a$ | $a$ | $a$ |
| 3 | 104 | 120 | 15 | $a$ | 24 |
| 4 | 55 | 28 | 53 | $a$ | 35 |
| 5 | 52 | 117 | 25 | 27 | 57 |
| 6 | 7 | 10 | 4 | 5 | 5 |

$a$ Insoluble.

Figure 3:
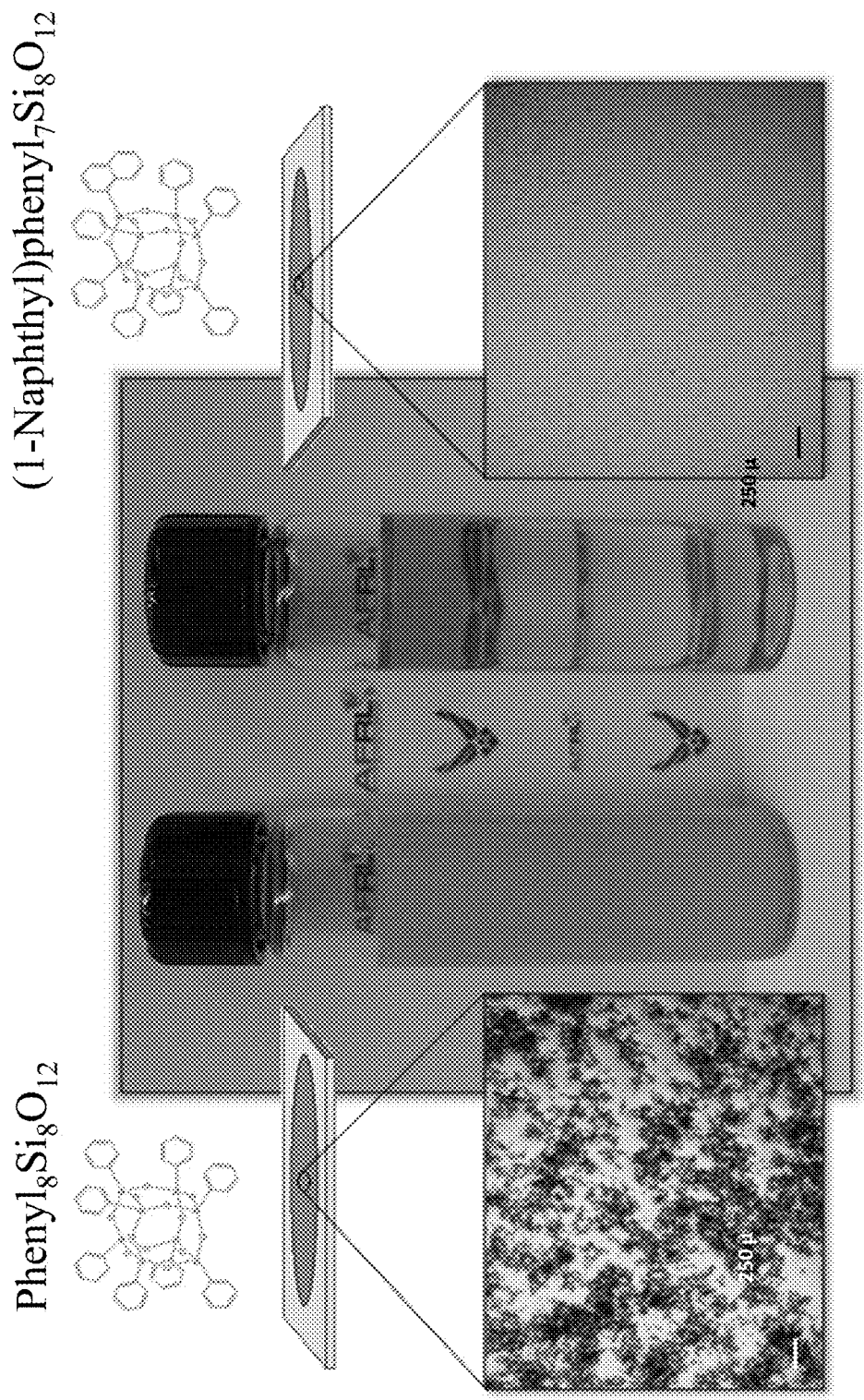
FIG. 3 compares photographs of PEI solutions containing symmetric $phenyl_8Si_8O_{12}$ with peripherally asymmetric (1-naphthyl)$phenyl_7Si_8O_{12}$ and optical micrographs of drop cast films from the two PEI solutions.

To examine the phase behavior of this new class of peripherally-asymmetric POSS nanoparticles with a representative aromatic polymer, attempts were made to solubilize both phenyl$_8$Si$_8$O$_{12}$ and (1-naphthyl)phenyl$_7$Si$_8$O$_{12}$ in polyetherimide (Ultem 1000, PEI). Chloroform solutions were prepared at a solute concentration of 5 weight percent PEI and POSS concentration of 5 weight percent with respect to PEI. Subsequent films from these solutions were drop cast onto glass substrates, dried under vacuum, and annealed at 220° C., above the glass transition temperature of PEI, to promote equilibrium phase formation. In accordance with the solubility study, the solution containing asymmetric (1-naphthyl)-phenyl$_7$Si$_8$O$_{12}$ is transparent, indicating superior solubility in chloroform, in contrast to that containing symmetric phenyl$_8$Si$_8$O$_{12}$, which is cloudy, as shown in FIG. 3.

Qualitatively, the dried and annealed films were visually observed to be of contrasting appearance. The film containing symmetric phenyl$_8$Si$_8$O$_{12}$ was significantly more opaque, indicating a greater degree of phase separation. Examination of the films by microscopy revealed aggregated particles of phenyl$_8$Si$_8$O$_{12}$ at length scales greater than 1 mm in some regions of the PEI host. Phase separation in the film containing (1-naphthyl)-phenyl$_7$Si$_8$O$_{12}$ appears to be limited to less than 5 microns in the post-annealed state, revealing improved solubility in the predominately aromatic polymer, shown in FIG. 3.

Replacing a single phenyl ring on phenyl$_8$Si$_8$O$_{12}$ with one of several polycyclic aromatic groups results in compounds that exhibit improved solubility in organic solvents and aromatic polymers, without significant sacrifices in thermal stability. These improvements, relative to the state-of-the-art materials, are realized through a disruption of symmetry and reduced ordering in the forms of crystallization and/or aggregation. These compounds offer new opportunities to blend ArPOSS with a variety of organic/polymer materials, a possibility that was previously impractical due to the insolubility of phenyl$_8$Si$_8$O$_{12}$.

Applications for this new class of ArPOSS compounds include, but are not limited to: the mechanical and thermal reinforcement of organic and preceramic polymers, protective coatings for organic substrates, and surfactants for the hybridization of organic and inorganic materials.

The following examples are examples of reduction to practice of the present invention and confirmation that the principles described in the present invention are therefore valid but should not be construed as in any way limiting the scope of the invention.

EXAMPLES

Materials

Phenyl$_7$Si$_7$O$_9$(OH)$_3$ was obtained from Hybrid Plastics, while additional silicon-containing organic compounds were purchased from Gelest. Remaining chemicals were purchased from Aldrich. All chemicals were used without further purification unless otherwise noted. All reactions were performed under an atmosphere of dry nitrogen. Flasks were oven-dried and allowed to cool under nitrogen prior to use.

Characterization $^1$H, $^{13}$C, and $^{29}$Si NMR spectra were obtained on Bruker 300-MHz and 400-MHz spectrometers using 5 mm o.d. tubes. Sample concentrations were approx. 10% (w/v) in chloroform-d. Combustion analysis was performed by Atlantic Microlab, Inc. Norcross, Ga. Thermogravimetric analysis (TGA) was performed on a TA Instruments 5000 using 5-10 mg of material, at a scan rate of 10° C./min under a nitrogen atmosphere.

General Synthesis of Chlorosilane Compounds

1-Naphthyltrichlorosilane

Under a dry nitrogen atmosphere, a solution of 1-bromonaphthalene (27.7 g, 0.134 mol) in THF (175 mL) was added slowly to a suspension of magnesium turnings (3.9 g, 0.16 mol) in THF (15 mL) that had previously been activated with an iodine crystal. After cooling to room temperature, this Grignard reagent was added via cannula to a THF (70 mL) solution of SiCl$_4$ (25.1 g, 0.148 mol) and stirred overnight. The mixture was evaporated to dryness, extracted with hexane, and filtered to remove Mg halide. The product was distilled at 120° C. under dynamic vacuum to give a 67% yield (23.6 g, 0.0902 mol) of product. $^1$H NMR (CDCl$_3$, ppm) 8.46 (dd, 1H), 8.21 (dd, J=6.8 Hz, J=1.2 Hz, 1H), 8.09 (d, J=8.4 Hz, 1H), 7.96 (d, J=7.6 Hz, 1H), 7.69 (t, 1H), 7.62 (t, 1H), 7.57 (t, 1H). $^{13}$C{$^1$H}NMR (CDCl$_3$, ppm) 135.51 (CH), 134.42 (C), 134.07 (CH), 133.58 (C), 129.37 (CH), 127.91 (C), 127.45 (CH), 127.16 (CH), 126.56 (CH), and 124.65 (CH). $^{29}$Si{$^1$H} (CDCl$_3$, ppm) −0.17 (s).

2-Naphthyltrichlorosilane

Yield 31%. $^1$H NMR (CDCl$_3$, ppm) 8.40 (s, 1H), 7.96 (d, 2H), 7.89 (d, 1H), 7.82 (dd, J=8.4 Hz, J=1.5 Hz, 1H), 7.62 (m, 2H). $^{13}$C{$^1$H}NMR (CDCl$_3$, ppm) 135.49 (CH), 135.06 (C), 132.28 (C), 128.90 (CH), 128.54 (C), 128.52 (CH), 128.34 (CH), 127.85 (CH), 127.34 (CH), and 127.02 (CH). $^{29}$Si{$^1$H} (CDCl$_3$, ppm) −0.87 (s).

9-Phenanthrenyltrichlorosilane

Yield 58%. $^1$H NMR (CDCl$_3$, ppm) 8.76 (m, 1H), 8.68 (d, J=8.4 Hz, 1H), 8.48 (s, 1H), 8.43 (m, 1H), 7.99 (dd, J=7.9 Hz, J=0.5 Hz, 1H), 7.75 (m, 3H), 7.67 (t, 1H). $^{13}$C{$^1$H} NMR (CDCl$_3$, ppm) 139.02 (CH), 132.30 (C), 131.36 (C), 130.48 (C), 130.10 (CH), 129.77 (C), 129.45 (CH), 128.18 (CH), 127.25 (CH), 127.19 (CH), 127.14 (CH), 126.77 (C), 123.49 (CH), and 122.56 (CH). $^{29}$Si{$^1$H} (CDCl$_3$, ppm) −0.51 (s).

1-Pyrenyltrichlorosilane

Under a dry nitrogen atmosphere, n-BuLi (10.6 mL, 1.6 M) in hexanes was added drop-wise to a cooled (−60° C.) solution of 1-bromopyrene (5.01 g, 0.018 mol) in THF/Et$_2$O (1:1) (80 mL) and stirred for 2 hours at −60° C. The solution was cooled to −90° C. and a THF solution of SiCl$_4$ (8.66 g, 0.051 mol) (10 mL) was added slowly and stirred for 24 hours at room temperature. The reaction mixture was evaporated to dryness, washed in Et$_2$O (100 mL), and filtered to remove any unreacted 1-bromopyrene and LiBr. The filtrate was collected and evaporated to dryness to give a 48% yield of 1-trichlorosilylpyrene, a yellow powder. $^1$HNMR (CDCl3, ppm) 8.66 (d, J=9.3 Hz, 1H), 8.59 (d, J=8.1 Hz, 1H), 8.30 (m, 5H), 8.11 (m, 2H). $^{13}$C{$^1$H}NMR (CDCl$_3$, ppm) 136.18 (C), 135.85 (C), 133.13 (CH), 132.06 (C), 131.30 (C), 131.22 CH), 130.31 (CH), 127.96 (CH), 127.67 (CH), 127.61 (CH), 126.65 (CH), 125.61 (C), 125.01 (CH), and 124.39 (C). $^{29}$Si{$^1$H} (CDCl$_3$, ppm) −1.64 (s).

General Synthesis of POSS Compounds

1-Naphthyl)phenyl$_7$Si$_8$O$_{12}$ (1-NapPh$_7$Si$_8$O$_{12}$)

Under a dry nitrogen atmosphere, phenyl$_7$Si$_7$O$_9$(OH)$_3$ (19.0 g, 0.0211 mol) was dissolved in THF (150 mL). A solution of 1-naphthyltrichlorosilane (5.63 g, 0.0215 mol) in THF (50 mL) was then slowly added. A dilute solution of triethylamine (6.84 g, 0.0676 mol) in THF (100 mL) was then added over a 90 min period under vigorous stirring. The reaction was allowed to proceed overnight. The solution was then filtered and the volume reduced under dynamic vacuum. The product was dissolved in ether and an aqueous wash (4:1)

was performed to remove water-soluble byproducts. The solution was again reduced under vacuum and the remaining oil was dissolved in THF. The solution was precipitated in methanol and then filtered to obtain a 92% yield of product (21.0 g, 0.0194 mol). $^1$H NMR (CDCl$_3$, ppm) 8.51 (m, 1H-nap), 8.04 (dd, J=6.8 Hz, J=1.3 Hz, 1H-nap), 7.98 (d, J=8.3 Hz, 1H-nap), 7.81 (m, 15H-nap/ph), 7.39 (m, 24H-nap/ph). $^{13}$C {$^1$H} NMR (CDCl$_3$, ppm) 136.45 (C-nap), 135.36 (CH-nap), 134.22, 134.21, 134.18 (3:1:3, CH-ph), 133.16 (C-nap), 131.51 (CH-nap), 130.83, 130.80, 130.77 (3:1:3, CH-ph), 130.17, 130.13, 0130.03 (3:1:3, C-ph), 128.65 (CH-nap), 128.34 (CH-nap), 128.23 (C-nap), 127.91, 127.88, 127.85 (3:1:3, CHph), 126.50 (CH-nap), 125.73 (CH-nap), and 124.83 (CH-nap). $^{29}$Si{$^1$H} (CDCl$_3$, ppm) −77.37, −78.05, −78.14, and −78.17 (1:3:1:3). Combustion Anal. (Calcd): C, 57.68 (57.64); H, 3.81 (3.91).

(2-Naphthyl)phenyl$_7$Si$_8$O$_{12}$ (2-NapPh$_7$Si$_8$O$_{12}$)

Yield 90%. $^1$H NMR (CDCl$_3$, ppm) 8.31 (s, 1H-nap), 7.84 (m, 18 Hnap/ph), 7.45 (m, 23H-nap/ph). $^{13}$C {$^1$H} NMR (CDCl$_3$, ppm) 135.91 (CH-nap), 134.51 (C-nap), 134.22 (CH-ph), 132.59 (C-nap), 130.82, 130.80 (3:4, CH-ph), 130.14 (C-ph), 129.58 (CH-nap), 128.46 (CHnap), 127.89 (CH-ph), 127.71 (CH-nap), 127.47 (C-nap), 127.29 (CHnap), 127.06 (CH-nap), and 126.03 (CH-nap). $^{29}$Si{$^1$H} (CDCl$_3$, ppm) −77.94, −78.14, and −78.18 (1:3:4). Combustion Anal. Calcd: C, 57.28 (57.64); H, 3.87 (3.91).

(9-Phenanthrenyl)phenyl$_7$Si$_8$O$_{12}$ (PhenPh$_7$Si$_8$O$_{12}$)

Yield 79%. $^1$H NMR (CDCl$_3$, ppm) 8.74 (d, J=7.6 Hz, 1H-phen), 8.68 (d, J=8.3 Hz, 1H-phen), 8.51 (dd, J ¼ 7.8 Hz, J ¼ 1.2 Hz, 1Hphen), 8.31 (s, 1H-phen), 7.84 (m, 15H-phen/ph), 7.64 (m, 4H-phen), 7.43 (m, 21H-ph). 13C {1H} NMR (CDCl$_3$, ppm) 138.35 (CH-phen), 134.24, 134.23 (3:4, CH-ph), 133.89 (C-phen), 131.66 (C-phen), 130.83 (CH-ph), 130.59 (C-phen), 130.18, 130.14, 130.03 (3:1:3, C-ph), 129.97 (C-phen), 129.21 (CH-phen), 127.91, 127.88 (3:4, CHph), 127.11 (C-phen), 126.86 (CH-phen), 126.60 (CH-phen), 126.43 (CH-phen), 122.92 (CH-phen), and 122.40 (CH-phen). $^{29}$Si{$^1$H} (CDCl$_3$, ppm) −77.28, −78.06, −78.12, and −78.18 (1:3:3:1). Combustion Anal. (Calcd): C, 59.10 (59.33); H, 3.84 (3.91).

(1-Pyrenyl)phenyl$_7$Si$_8$O$_{12}$ (PyPh$_7$Si$_8$O$_{12}$)

Yield 29%. $^1$H NMR (CDCl$_3$, ppm) 8.72 (d, J=9.2 Hz, 1H-py), 8.43 (d, J=7.6 Hz, 1H-py), 8.21 (m, 2H-py), 8.12 (m, 3H-py), 8.04 (m, 2H-py), 7.80 (m, 14H-ph), 7.37 (m, 21H-ph). $^{13}$C {1H} NMR(CDCl3, ppm) 136.09 (py-C), 134.29, 134.24 (3:4, CH-ph), 133.34 (py-C), 33.30 (py-CH), 131.14 (py-C), 130.87, 130.81 (4:3, CH-ph), 130.74 (py-C), 130.24, 130.20, 130.10 (3:1:3, C-ph), 128.66 (py-CH), 128.11 (py-CH), 127.95, 127.91 (3:4, CH-ph), 127.78 (py-CH), 127.47 (py-CH), 125.91 (py-CH), 125.59 (py-CH), 125.42 (py-CH), 125.27 (py-C), 124.60 (py-C), 124.50 (py-C), and 124.04 (py-CH). 29Si{1H} (CDCl3, ppm) −76.80, −77.82, and −77.93 (1:3:4). Combustion Anal. (Calcd): C, 59.77 (60.18); H, 3.75 (3.83).

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

The invention claimed is:

1. A method of synthesizing a peripherally asymmetric aryl polyhedral oligomeric silsesquioxane (ArPOSS) compound having a structure:

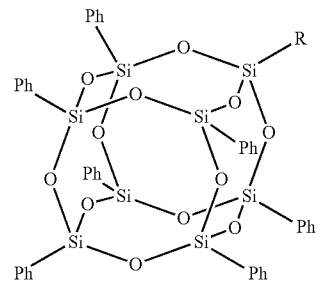

wherein Ph is phenyl and wherein R is selected from the group consisting of 1-Naphthyl, 2-Naphthyl, 9-Anthracenyl, 9-Phenanthrenyl, and 1-Pyrenyl, the method comprising:
reacting an uncondensed phenyl POSS with a trichlorosilane via a capping reaction, the uncondensed phenyl POSS having a structure:

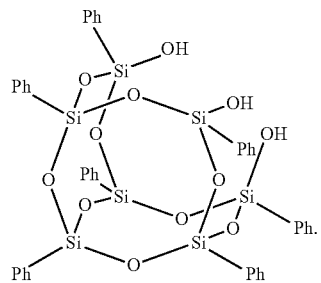

2. A method of improving solubility of a functionalized polyhedral oligomeric silsesquioxane compound, the method comprising:
corner-capping an uncondensed phenyl polyhedral oligomeric silsesquioxane with a chlorosilane having a terminal aryl group or a chlorosilane having a polycyclic aromatic functional group.

3. The method of claim 2, further comprising:
preparing the chlorosilane having the terminal aryl group by reacting an aryl Grignard or a lithium reagent with silicon tetrachloride.

4. The method of claim 2, wherein the method is carried out under basic conditions.

5. A method of synthesizing a peripherally asymmetric aryl polyhedral oligomeric silsesquioxane (ArPOSS) compound, the method comprising:

corner-capping an uncondensed phenyl-POSS alcohol using a chlorosilane having a terminal aryl group or a chlorosilane having a polycyclic aromatic functional group, the terminal aryl group or the polycyclic aromatic functional group being geometrically larger than the phenyl groups of the phenyl-POSS alcohol.

6. The method of claim 5, further comprising:

preparing the chlorosilane having the terminal aryl group by reacting an aryl Grignard or a lithium reagent with silicon tetrachloride.

7. The method of claim 5, wherein the method is carried out under basic conditions.

8. The method of claim 5, wherein the terminal aryl group is selected from the group consisting of 1-Naphthyl, 2-Naphthyl, 9-Anthracenyl, 9-Phenanthrenyl, and 1-Pyrenyl.

9. The method of claim 2, wherein the terminal aryl group or the polycyclic aromatic functional group is geometrically larger than phenyl groups of the polyhedral oligomeric silsesquioxane.

10. The method of claim 1, further comprising:

preparing the chlorosilane having the terminal aryl group by reacting an aryl Grignard or a lithium reagent with silicon tetrachloride.

11. The method of claim 1, wherein the method is carried out under basic conditions.

12. A method of synthesizing a peripherally asymmetric aryl polyhedral oligomeric silsesquioxane (ArPOSS) compound having a structure:

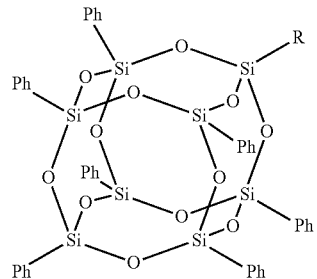

wherein Ph is phenyl and wherein R is a terminal aryl group that is geometrically larger than phenyl, the method comprising:

reacting an uncondensed phenyl POSS alcohol with a trichlorosilane via a capping reaction.

13. The method of claim 12, wherein the trichlorosilane is selected from the group consisting of 1-Naphthyl-trichlorosilane, 2-Naphthyl-trichlorosilane, 9-Anthracenyl-trichlorosilane, 9-Phenanthrenyl-trichlorosilane, and 1-Pyrenyl-trichlorosilane.

14. The method of claim 12, wherein the terminal aryl group is selected from the group consisting of naphthylene, anthracene, phenanthrene, and pyrene.

15. The method of claim 12, wherein the capping reaction is conducted in the presence of a base.

16. The method of claim 15, wherein the base is trimethylamine.

* * * * *